(12) United States Patent
Gray et al.

(10) Patent No.: US 7,862,577 B2
(45) Date of Patent: Jan. 4, 2011

(54) TEMPORARY VASCULAR FILTER GUIDE WIRE

(75) Inventors: William Gray, Marcer Island, NM (US); Richard A. Gambale, Tyngsboro, MA (US)

(73) Assignee: C. R. Bard, Inc., Murray Hill, NJ (US)

( * ) Notice: Subject to any disclaimer, the term of this patent is extended or adjusted under 35 U.S.C. 154(b) by 1282 days.

(21) Appl. No.: 10/255,232

(22) Filed: Sep. 25, 2002

(65) Prior Publication Data

US 2003/0074019 A1    Apr. 17, 2003

Related U.S. Application Data

(63) Continuation of application No. 09/457,203, filed on Dec. 6, 1999, now Pat. No. 6,461,370, which is a continuation of application No. PCT/US98/23516, filed on Nov. 3, 1998, which is a continuation of application No. 08/963,524, filed on Nov. 3, 1997, now abandoned.

(51) Int. Cl.
*A61F 2/01* (2006.01)

(52) U.S. Cl. ....................................... 606/200

(58) Field of Classification Search ................. 606/200; 623/1.1
See application file for complete search history.

(56) References Cited

U.S. PATENT DOCUMENTS

| | | | |
|---|---|---|---|
| 3,540,431 A | 11/1970 | Mobin-Uddin | |
| 4,577,631 A | 3/1986 | Kreamer | |
| 4,619,246 A | 10/1986 | Molgaard-Nielsen et al. | |
| 4,643,184 A | 2/1987 | Mobin-Uddin | |
| 4,650,466 A | 3/1987 | Luther | |
| 4,723,549 A | 2/1988 | Wholey et al. | |
| 4,727,873 A | 3/1988 | Mobin-Uddin | |
| 4,790,812 A | 12/1988 | Hawkins, Jr. et al. | |
| 4,790,813 A | 12/1988 | Kensey | |
| 4,794,928 A | 1/1989 | Kletschka | |
| 4,817,600 A | 4/1989 | Herms et al. | |

(Continued)

FOREIGN PATENT DOCUMENTS

AU    A 67827/87    1/1987

(Continued)

OTHER PUBLICATIONS

*Release of Atherosclerotic Debris After Transluminal Angioplasty*, Peter C. Block, M.D., David Elmer, and John T. Fallon, M.D., Ph.D., vol. 65, No. 5, May 1982.

*Primary Examiner*—Anhtuan T Nguyen
*Assistant Examiner*—Ryan J Severson
(74) *Attorney, Agent, or Firm*—Rutan & Tucker, LLP

(57) ABSTRACT

A temporary filter is described for use in percutaneous intravascular procedures for the treatment of diseased blood vessels, such as angioplasty or stent placement procedures. The guide wire which is used to direct a catheter (such as a balloon catheter) to a treatment site contains a deployable filter. The guide wire is moveable independently of the catheter and can be used to position the filter at a desired location downstream of the treatment site. The guide wire includes parts moveable with respect to each other and the filter is connected to these parts in such a way that it can be deployed and collapsed by relative movement of the parts.

32 Claims, 8 Drawing Sheets

U.S. PATENT DOCUMENTS

| | | |
|---|---|---|
| 4,842,579 A | 6/1989 | Shiber |
| 4,873,978 A | 10/1989 | Ginsburg |
| 4,885,003 A * | 12/1989 | Hillstead ..................... 604/22 |
| 4,921,478 A | 5/1990 | Solano et al. |
| 4,926,858 A | 5/1990 | Gifford, III et al. |
| 4,943,297 A | 7/1990 | Saveliev et al. |
| 4,950,238 A | 8/1990 | Sullivan |
| 4,969,891 A | 11/1990 | Gewertz |
| 4,979,951 A | 12/1990 | Simpson |
| 5,041,093 A * | 8/1991 | Chu ........................... 604/104 |
| 5,092,839 A | 3/1992 | Kipperman |
| 5,108,419 A | 4/1992 | Reger et al. |
| 5,112,347 A | 5/1992 | Taheri |
| 5,147,379 A | 9/1992 | Sabbaghian et al. |
| 5,152,777 A | 10/1992 | Goldberg et al. |
| 5,154,724 A | 10/1992 | Andrews |
| 5,160,342 A | 11/1992 | Reger et al. |
| 5,324,304 A | 6/1994 | Rasmussen |
| 5,329,942 A | 7/1994 | Gunther et al. |
| 5,354,310 A | 10/1994 | Garnic et al. |
| 5,397,331 A | 3/1995 | Himpens et al. |
| 5,549,626 A | 8/1996 | Miller et al. |
| 5,662,671 A | 9/1997 | Barbut et al. |
| 5,695,518 A | 12/1997 | Laerum |
| 5,695,519 A | 12/1997 | Summers et al. |
| 5,720,764 A | 2/1998 | Naderlinger |
| 5,769,816 A | 6/1998 | Barbut et al. |
| 5,779,716 A | 7/1998 | Cano et al. |
| 5,795,322 A | 8/1998 | Boudewijn |
| 5,810,874 A | 9/1998 | Lefebvre |
| 5,814,064 A | 9/1998 | Daniel et al. |
| 5,827,324 A | 10/1998 | Cassell et al. |
| 5,876,367 A | 3/1999 | Kaganov et al. |
| 5,910,154 A | 6/1999 | Tsugita et al. |
| 5,911,734 A | 6/1999 | Tsugita et al. |
| 5,928,260 A | 7/1999 | Chin et al. |
| 5,941,896 A | 8/1999 | Kerr |
| 5,972,019 A | 10/1999 | Engelson et al. |
| 6,001,118 A | 12/1999 | Daniel et al. |
| 6,027,520 A | 2/2000 | Tsugita et al. |
| 6,042,598 A | 3/2000 | Tsugita et al. |
| 6,059,814 A | 5/2000 | Ladd |
| 6,066,158 A * | 5/2000 | Engelson et al. ............ 606/200 |
| 6,165,200 A | 12/2000 | Tsugita et al. |
| 6,245,089 B1 | 6/2001 | Daniel et al. |
| 6,258,115 B1 | 7/2001 | Dubrul |
| 6,676,682 B1 | 1/2004 | Tsugita et al. |
| 6,964,673 B2 | 11/2005 | Tsugita et al. |

FOREIGN PATENT DOCUMENTS

| | | |
|---|---|---|
| EP | 0 533 511 A | 3/1993 |
| FR | 2 567 405 A | 1/1986 |
| WO | WO 95 34254 A | 12/1995 |
| WO | WO 96/01591 A | 1/1996 |
| WO | WO/98/33443 A1 | 8/1998 |

* cited by examiner

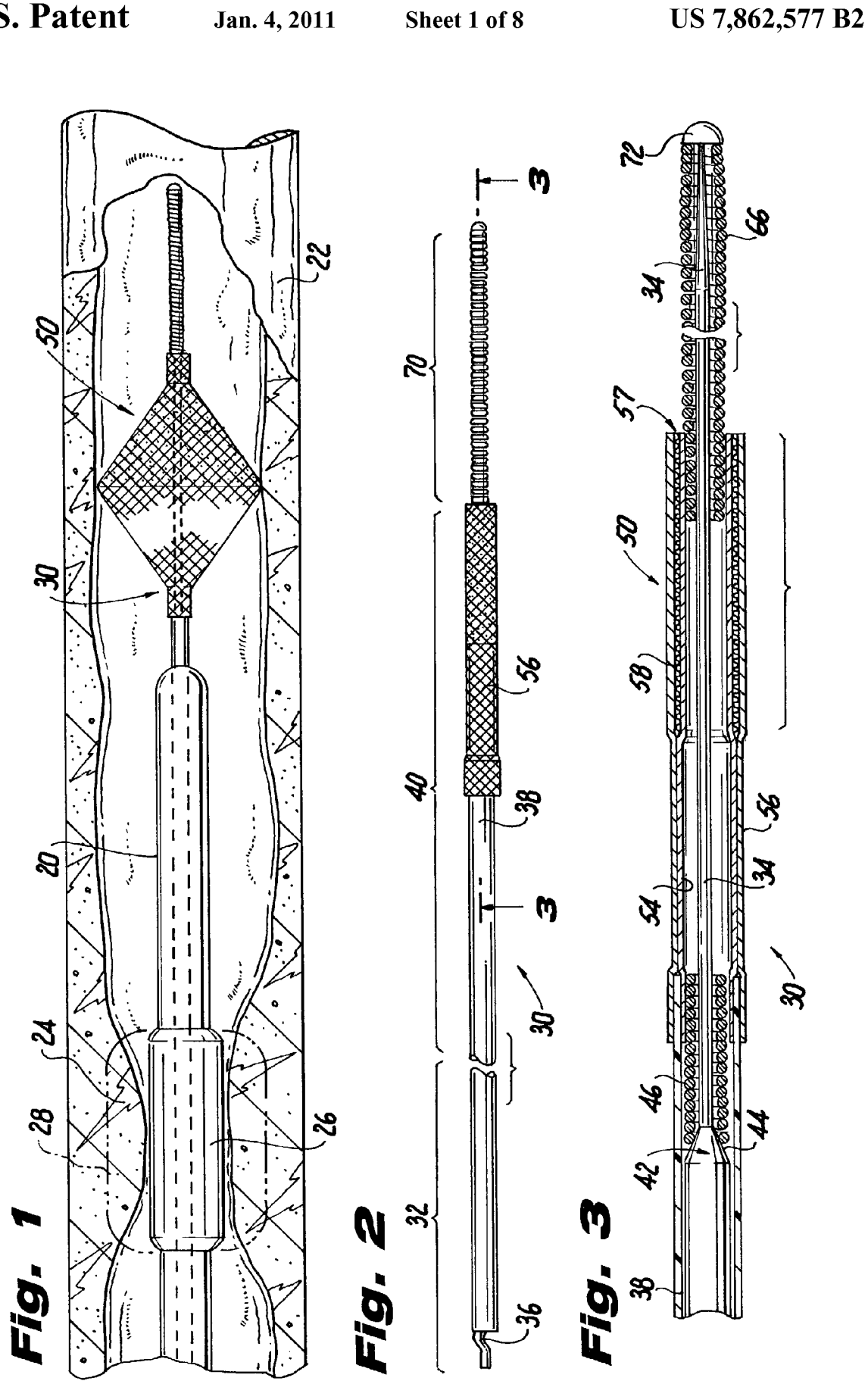

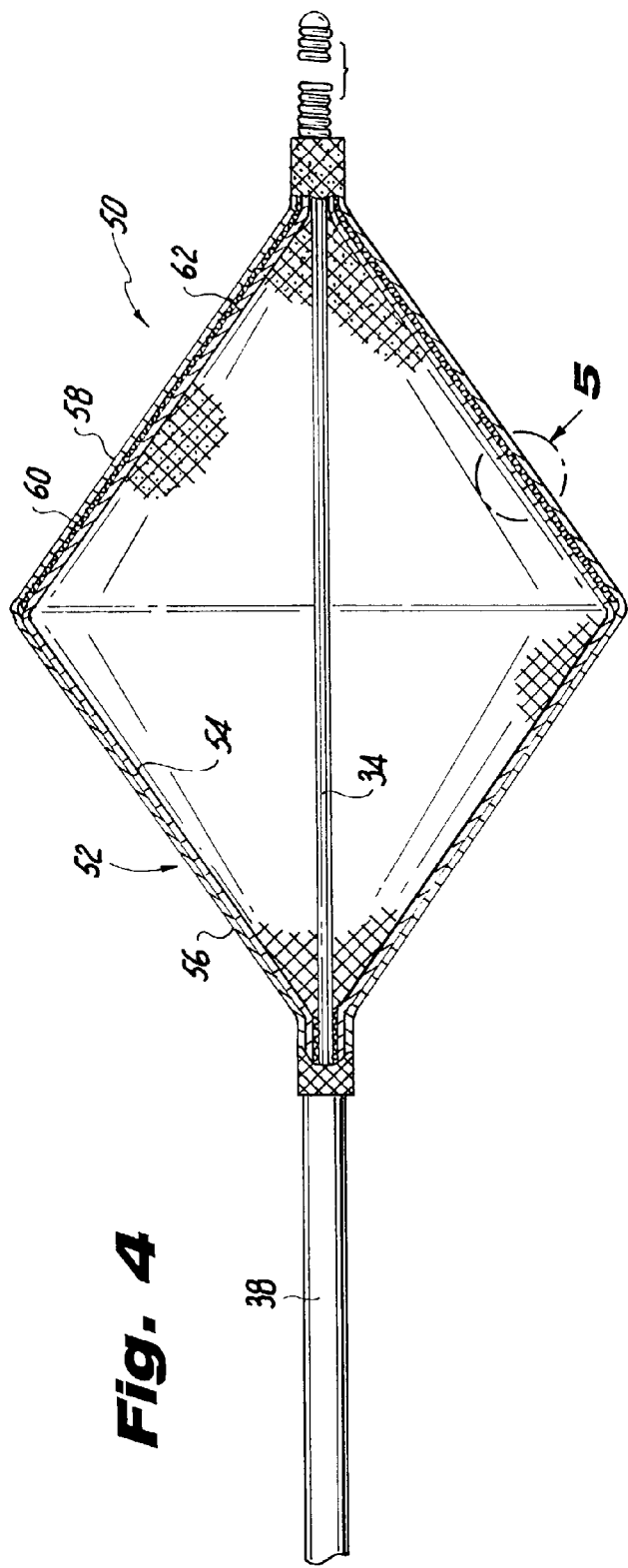
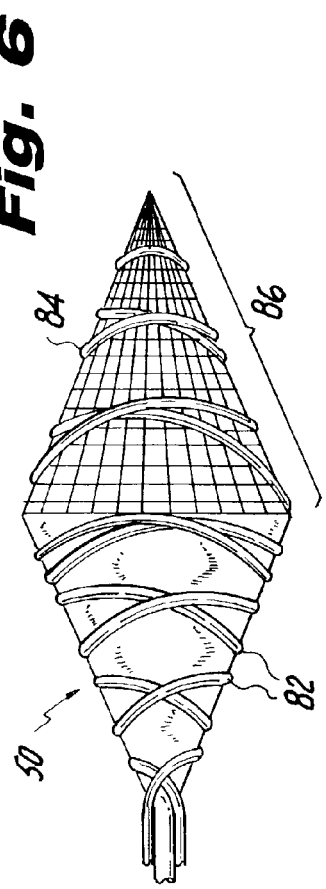
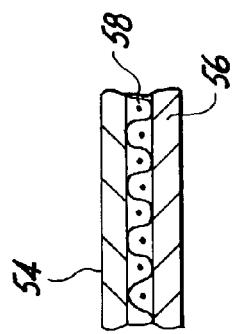

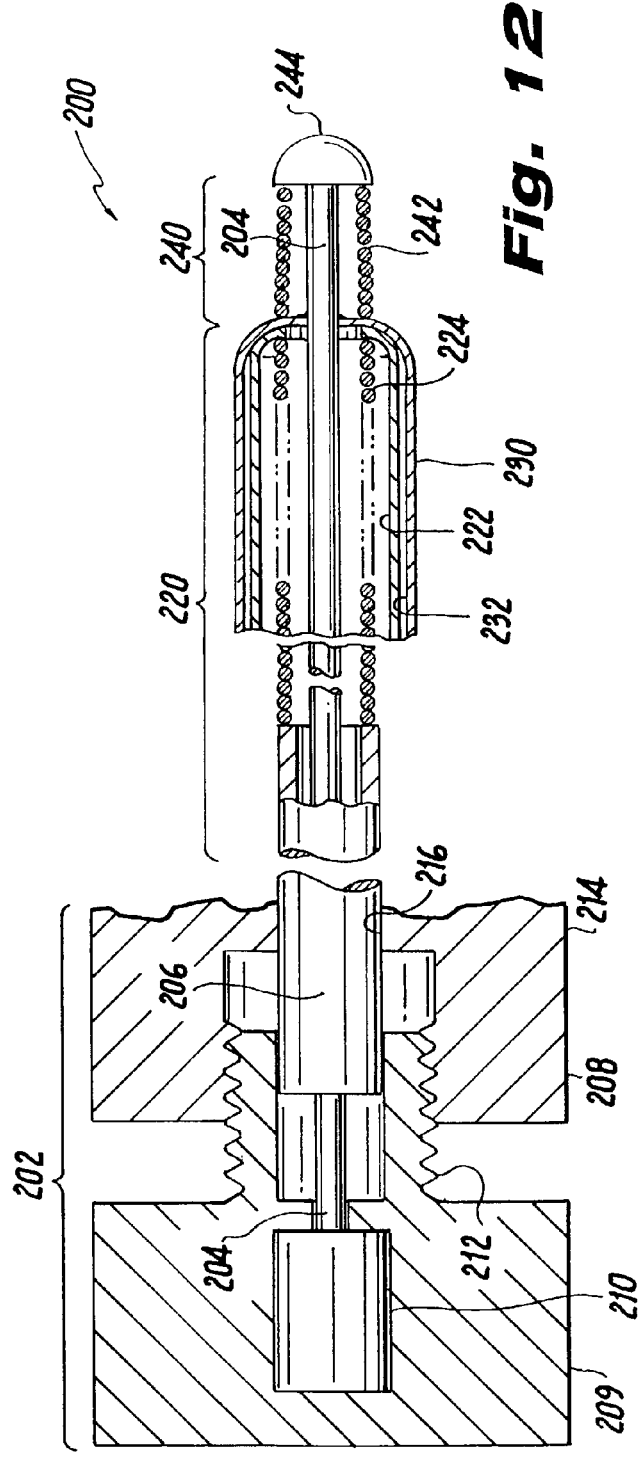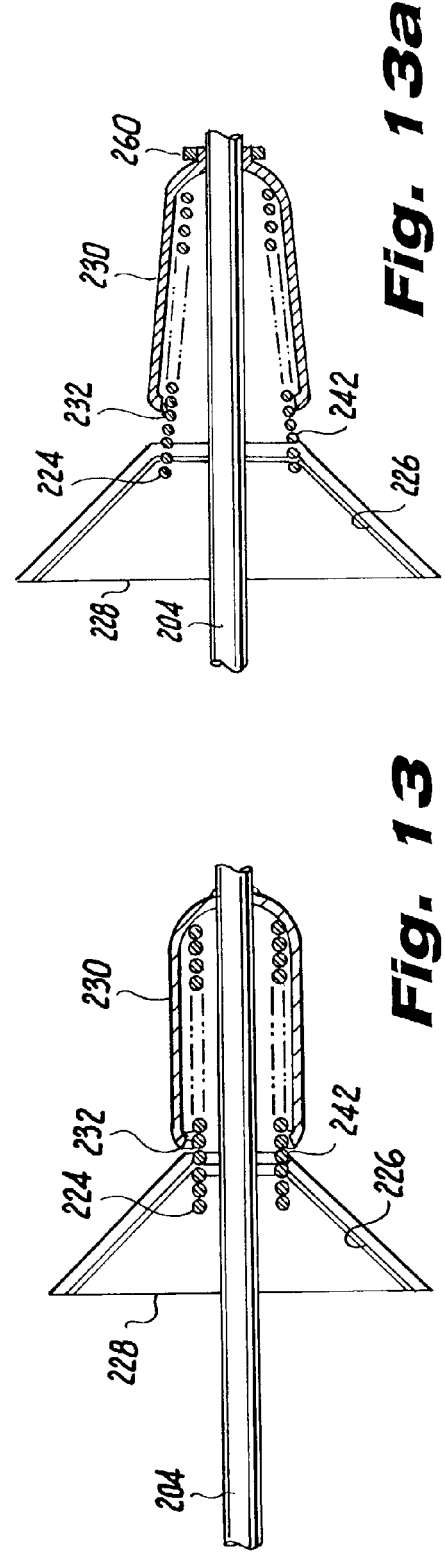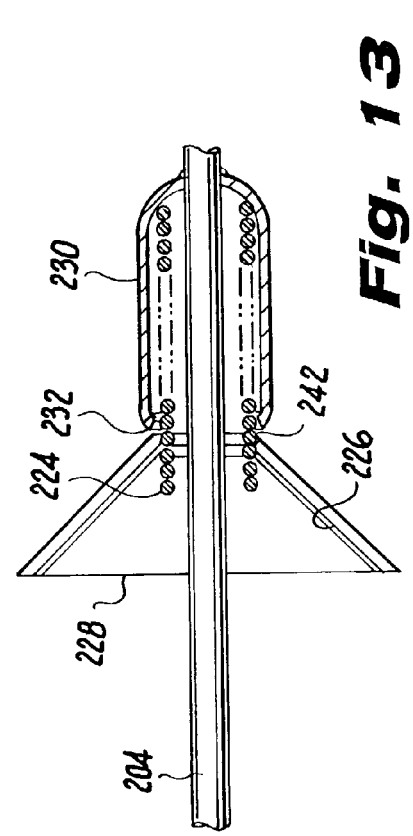

TEMPORARY VASCULAR FILTER GUIDE WIRE

This is a continuation of application Ser. No. 09/457,203, filed Dec. 6, 1999, now U.S. Pat. No. 6,461,370 which is a continuation of application Serial No. PCT/US98/23516, filed Nov. 3, 1998, which is a continuation of application Ser. No. 08/963,524, filed Nov. 3, 1997, now abandoned. Each of these prior applications is hereby incorporated herein by reference, in its entirety.

FIELD OF THE INVENTION

The invention relates to vascular filters intended to capture embolic particles, by means of filtration, that may arise from the treatment of diseased blood vessels.

BACKGROUND OF THE INVENTION

Percutaneous intravascular treatment of diseased blood vessels, such as angioplasty or stent placement procedures, may result in the dislodgment of loose plaque or thrombus which then migrate downstream. Since any such particles may become lodged in other vessels, effectively preventing blood from passing into the organ which that vessel supplies, and potentially causing serious end-organ damage which may be difficult or impossible to reverse, effective avoidance of this complication is extremely important.

One of the early methods of removing residual matter resulting from an angioplasty procedure using a balloon catheter involved maintaining the balloon in an inflated state while performing the intended intervention on the blood vessel. In this manner, much of the material could be removed without an extraneous filtering device. However, the reliability of such a procedure, especially for blood vessels supplying oxygen to the brain, necessitated substantial improvement.

Previous attempts at vascular filters have included a vena caval filter, which is permanently deployed in the vena cava via a peripheral vein in order to prevent embolisation of blood clots from the veins of the legs to the lungs, thus avoiding potentially serious and life threatening pulmonary embolism. The filter typically included a plurality of anchoring legs bent outwardly to form hooks to penetrate the vessel wall and secure the filter permanently in position. An example of such a device is disclosed in U.S. Pat. No. 4,619,246.

While conventional vena caval filters work well for their intended purposes, they suffer from the disadvantages associated with damaging the inner vessel wall through the inherent penetrating nature of the hooks, and blockage caused over time as the filter becomes endothelialized with the blood vessel inner wall or as recurrent blood clots obstruct blood flow through the filter.

In an effort to resolve the problems with vena caval filters, those skilled in the art have developed temporary filtering mechanisms that attach to an angioplasty catheter and withdraw from the vasculature following the procedure. One proposal, disclosed in U.S. Pat. No. 4,723,549, discloses a collapsible wire mesh filter disposed around the distal portion of a wire guided balloon catheter. A filter balloon is positioned beneath the wire mesh and inflates radially outwardly to expand the wire mesh when inserted downstream of a stenosed blood vessel. As the vessel is treated, fine particles dislodged from the stenosis are trapped by the mesh and subsequently removed with the filter and catheter following the procedure.

A similar device and method, disclosed in U.S. Pat. No. 4,873,978 includes a balloon catheter directed through a vasculature by a guide wire. The catheter mounts a strainer at its distal end that responds to actuation of a separate control wire to open and close a plurality of tines capable of retaining dislodged particles from a treated stenosis.

The temporary filter devices described above require additional lumens and/or control wires beyond those associated with the catheter guide wire to control the filtering procedure. The extra lines and wires typically create added complexity for the operator. Moreover, it is often desirable to adjust the relative spacing between the deployed filter and the stenosed area due to the potential presence of additional blood vessels proximate the stenosis. Because the conventional filters are mounted to the distal ends of the respective catheters, adjustments during the procedure typically cannot be made. Furthermore, the use of balloon catheters and stent devices involving the same procedure could not be achieved with filter protection in place.

Therefore, a need exists in the art for a temporary vascular filter which does not require additional control wires and catheter lumens. Moreover, the need exists for such a filter in which adjustment of the filter with respect to a lesioned vessel area, and allows for the exchange of various types of devices (e.g., balloon catheters, stents, etc.), while maintaining protection against distal emboli. The temporary vascular filter guide wire of the present invention satisfies these needs.

SUMMARY OF THE INVENTION

The apparatus and method of the present invention minimizes the complexity associated with manipulating a vascular filter during an angioplasty or stent placement procedure by incorporating the filter on a catheter guide wire such that the guide wire performs the dual functions of guiding the catheter to a stenosed location, and filtering dislodged particles flowing downstream of the treated area. Moreover, because the guide wire operates independently of the catheter, relative spacing between the filter and the lesion location may be easily altered, and exchanges of various devices over the wire are possible.

To realize the advantages described above, the invention, in one form, comprises a vascular filter guide wire for directing precision placement of a catheter or stent proximate a lesion and selectively filtering particulate debris dislodged by treatment. The guide wire includes an actuating mechanism and an elongated flexible core wire having a proximal end mounted to the actuating mechanism and a distal end for insertion through a vasculature to a position downstream of the lesion. A tubular flexible shaft is slidably disposed telescopically along the core wire. The shaft includes a proximal portion affixed to the actuating mechanism in movable relation to the wire proximal end, and a distal portion disposed inwardly from the core wire distal end for placement downstream of the lesion. A collapsible strainer coupled to the shaft distal portion is operable, in response to relative displacement between the shaft and the core wire, to radially extend outwardly within the vasculature so that it can trap particulate matter arising from the treatment of the lesion.

In another form, the invention comprises a catheter system for treating a lesion within the vasculature. The catheter system includes a catheter having a lesion treatment device and a vascular filter guide wire for directing the catheter to the lesion. The guide wire includes a collapsible filter for deployment downstream of the catheter to trap particulate matter dislodged from the lesion during the treatment.

In yet another form, the invention comprises a method of filtering particulate debris from a vasculature caused by treatment of a lesion with a catheter having a lesion treatment portion, the catheter being guided to the location of the lesion by a vascular filter guide wire having a core wire, a slidable shaft, and a collapsible filter mounted on the shaft and deployable upon relative displacement between the core wire and the shaft. The method includes the steps of first guiding the vascular filter guide wire through the vasculature along a predetermined path to a lesion such that the filter is disposed downstream of the lesion. The next step involves deploying the filter radially outwardly by shifting the shaft relative to the core wire. Then, the catheter is run over the guide wire along the predetermined path to position the lesion treatment portion of the catheter proximate the lesion. The method continues by treating the lesion according to a predetermined procedure then maintaining the filter in a deployed position until the risk of particulate matter is substantially eliminated. The catheter is then withdrawn from the vasculature and the filter retracted radially inwardly by shifting the shaft back to the original position. The method then concludes with the step of removing the guide wire from the vasculature.

One embodiment of the invention comprises a vascular filter for controllably expanding within a blood vessel to trap particulate matter loosened from treatment of a lesion. The filter is responsive to relatively shiftable control elements to expand and retract and includes a braid comprising a composite metallic/polymeric material. The material includes a plurality of metallic filaments mounted to the respective shiftable shaft and core wire to define a support structure and a polymeric mesh interwoven with the metallic filaments to define a strainer.

Another form of the invention comprises a method of fabricating a vascular filter. The method includes the steps of first selecting a mandrel having a plurality of consecutively connected forms and weaving a continuous layer of braid over the consecutively connected forms. The method proceeds by bonding the braid filaments at spaced apart sections between respective forms and separating the respective braided forms at the bonded sections. The forms are then removed from the layer of braid.

Other features and advantages of the present invention will be apparent from the following detailed description when read in conjunction with the accompanying drawings.

BRIEF DESCRIPTION OF THE DRAWINGS

FIG. 1 is an enlarged, partial sectional view of a catheter system of the present invention deployed within a blood vessel;

FIG. 2 is a partial longitudinal view of a guide wire in a retracted position according to a first embodiment of the present invention;

FIG. 3 is a partial longitudinal sectional view along line 3-3 of FIG. 2;

FIG. 4 is a partial longitudinal sectional view similar to FIG. 3 but in a deployed orientation;

FIG. 5 is an enlarged view of detail 5-5;

FIG. 6 is a longitudinal view of a filter construction according to an alternative embodiment of the present invention;

FIG. 12 is a partial longitudinal sectional view of a guide wire in a retracted state according to a second embodiment of the present invention;

FIG. 13 is a partial view of the guide wire of FIG. 12 in an extended state;

FIG. 13a is an alternative embodiment of the FIG. 13 which is frusto-conical in shape, according to an alternative embodiment of the present invention;

DETAILED DESCRIPTION OF THE INVENTION

Figure 7:
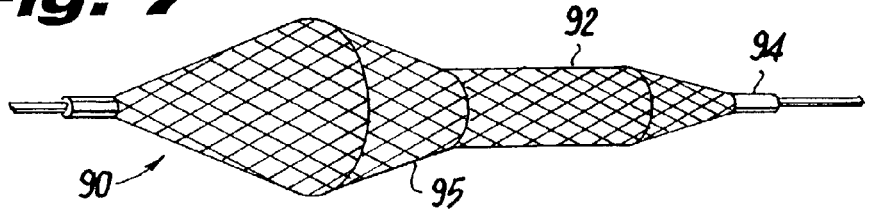
FIG. 7 is a longitudinal view of a filter construction according to yet another embodiment of the present invention.

With reference to FIG. 1, percutaneous angioplasty or stent placement techniques enable operators to minimize trauma often associated with more invasive surgical techniques. This is possible through the use of a thin catheter 20 that advances through the vascular system to a predetermined blood vessel 22 having a lesion such as a stenosis 24 blocking the flow of blood therethrough. Typically, the catheter includes a lesion treatment device such as a balloon 26 or stent (not shown) for positioning coaxially within the lesion. Once positioned, the balloon or stent radially expands, as shown at 28, to exert a radially outwardly directed force against the material and initiate dilation thereof.

In order to reach the lesioned area, however, the catheter must be able to follow a trackable path defined by a catheter guide wire. In accordance with a first embodiment of the present invention, a catheter guide wire, generally designated 30, provides a trackable path for a catheter and includes a distally disposed collapsible filter 50 to trap particulate matter dislodged by the catheter 20 during treatment of the stenosis.

Referring now to FIGS. 2 through 5, the guide wire 30 includes a proximal section 32 comprising a solid core wire 34 having a wave-shaped proximal end 36 (FIG. 2). A tubular shaft 38 is coaxially disposed around the core wire and includes an outer diameter equal to the nominal size of the guide wire. The inner diameter of the shaft is sized to form a friction fit with the core wire proximal end when slid thereover during insertion and removal of the guide wire. The shaft functions to deploy and retract the filter device, to guide and support the catheter 20, and to smoothly transmit rotation from the proximal section 32 to an intermediate section 40. Preferably, the shaft comprises a polyimide tube or hypotube. In some applications, where relatively long lengths are required, an extension (not shown) may be attached to the proximal section to increase the length up to three meters.

The intermediate section 40 extends axially from the proximal section 32 and generally comprises an extension of the shaft 38 to coaxially surround the core wire 34. The core wire is formed distally with a primary tapered portion 42 defining an annular shoulder 44 for mounting a coiled spring 46.

With further reference to FIGS. 2 through 5, the filter 50 comprises a braided basket 52 having respective inner and outer braid layers 54 and 56 (FIG. 5) that, in one embodiment, serve as supports for a fine filter mesh 58. The supports expand the basket radially outwardly with the filter axial ends compressed inwardly, and radially retract the basket with the ends tensioned outwardly. The fine mesh 58 (FIG. 5) is interposed between the inner and outer supports along a distal-half portion 60 of the basket to prevent particulate matter from flowing through the blood vessel downstream of the treated stenosis. It is contemplated that the size of the pores of mesh 58 may be in the range of 40 to 500 microns. The meshed distal-half of the filter forms a collection cavity 62 for the material such that when retracted, the material is prevented from escaping the filter.

The proximal end of the filter basket is bonded (e.g. adhesively or by soldering) to the shaft 38 which may be inserted between braid layers 54 and 56.

The distal extremity 57 of basket abuts a flexible 30 coil spring 66 that coaxially surrounds the tip of the core wire 34. The core wire distal tip is tapered and the guide wire distal end terminates in a hemispherically shaped tip 72 which is bonded (e.g., by soldering) to the core wire distal tip. The guide wire distal end may be preformed into a "J" configuration (not shown) to aid in advancing the guide wire 30 through the vasculature.

With particular reference to FIG. 6, the preferred embodiment of filter 50 according to the present invention includes a braid comprising a composite metallic/polymeric material, eliminating the necessity of a separate mesh layer. In such an embodiment, a plurality of metallic filaments 82 provide structural support to the assembly for deploying and collapsing the filter. Polymeric filaments 84 are located on the distal half of the braid only, to provide a filtration cone 86. The dual materials, braided simultaneously, provide a pic density which will result in filtration spacing of approximately 40 to 500 microns for filtration, at a metal to polymeric ratio of approximately 1:4.

Figure 7A:
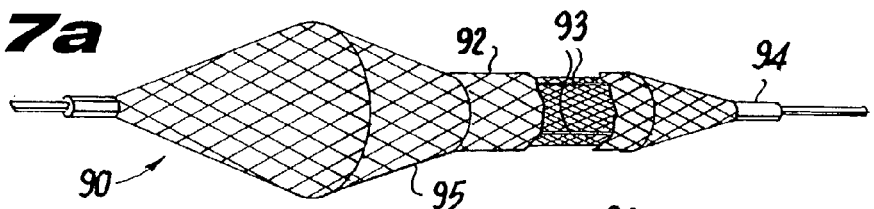
FIG. 7a is a cut-away portion of the FIG. 7 filter construction which illustrates longitudinal pleats, according to the FIG. 7 embodiment of the present invention.

In yet another embodiment of a filter according to the present invention, generally designated 90 and illustrated in FIG. 7, the filtering medium is wrapped in a cylinder 92 with a closed distal end 94 and a flared proximal end 95. Flaring of the proximal end may be effected by applying heat and pressure to the material thereby increasing the surface area and causing the material to bow radially outwardly. The cylinder is formed with longitudinal pleats 93 (shown in FIG. 7a) that are more flexible and collapsible than a straight cone configuration.

Figure 8:
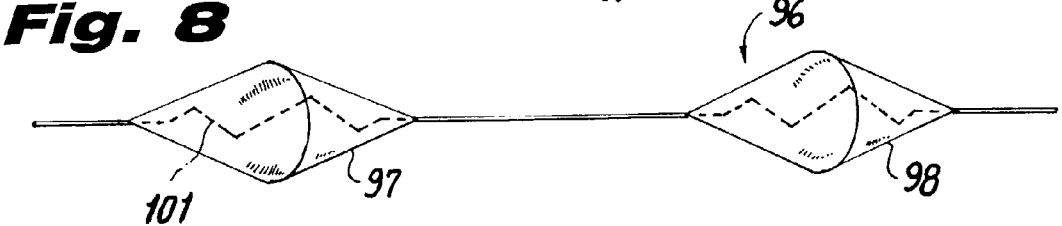
FIG. 8 is a mandrel system for use in the method of the present invention.
Figure 9:
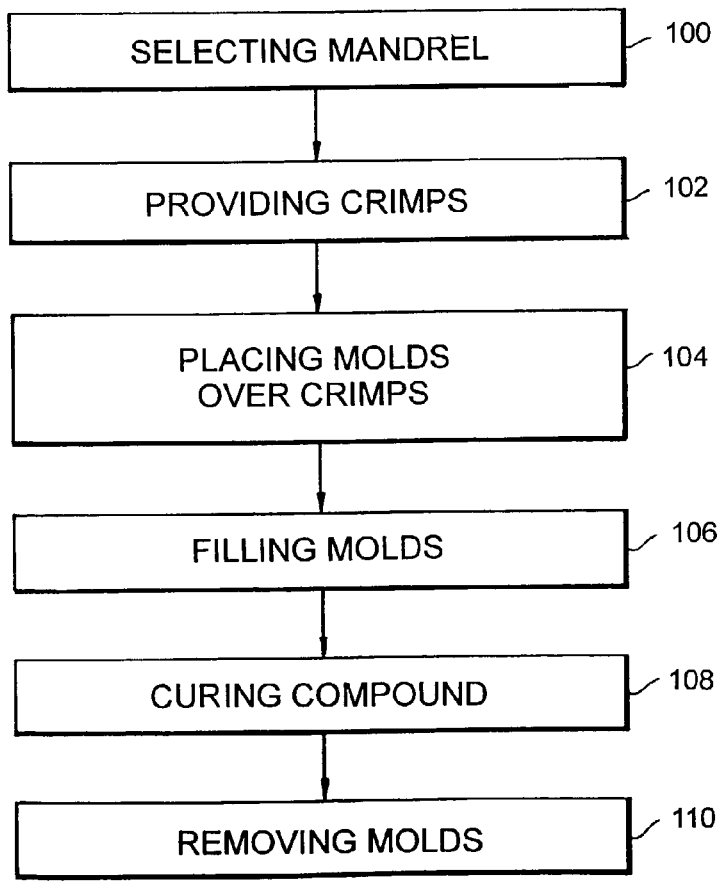
FIG. 9 is a block diagram illustrating steps in preparing the mandrel of FIG. 8.
Figure 10:
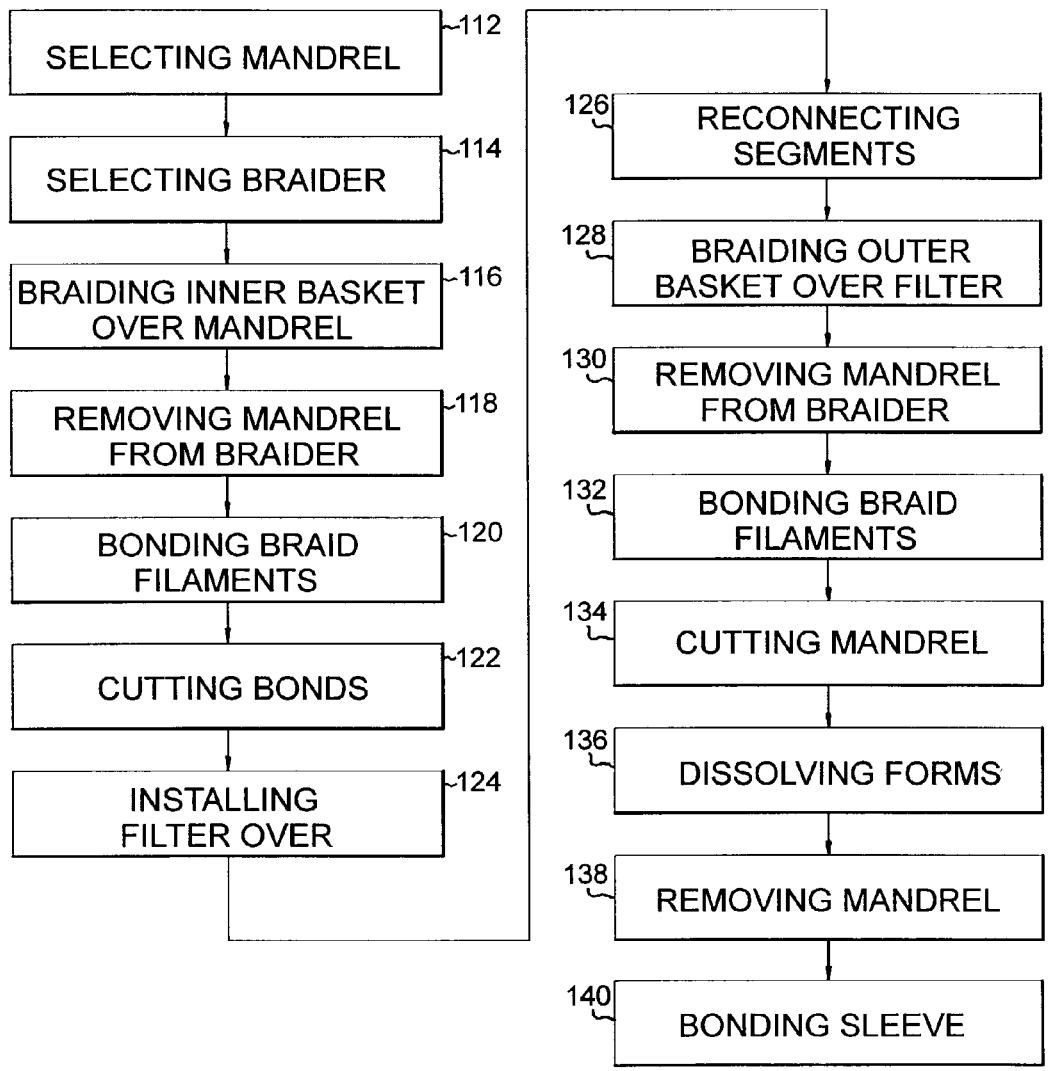
FIG. 10 is a block diagram illustrating steps in fabricating the filter of the present invention.
Figure 11A:
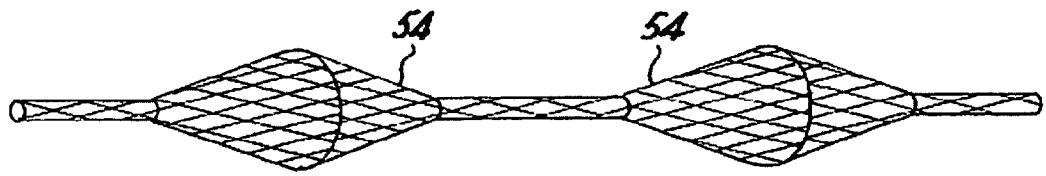
FIG. 11a-11g are views of various stages of construction corresponding to the steps of FIG. 10.
Figure 11B:
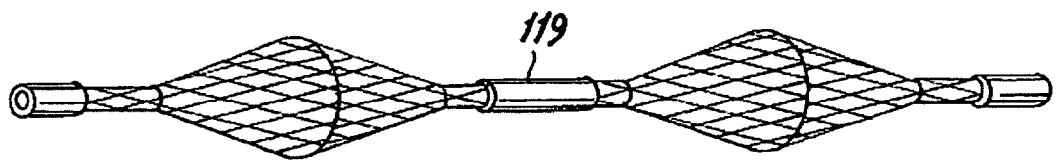
Figure 11C:
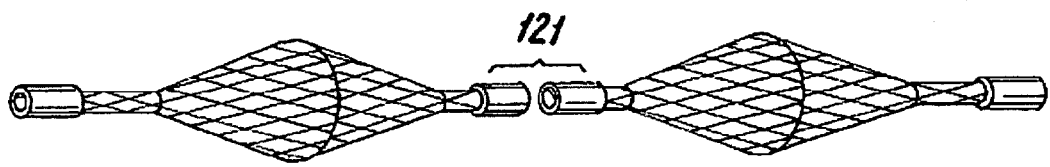
Figure 11D:
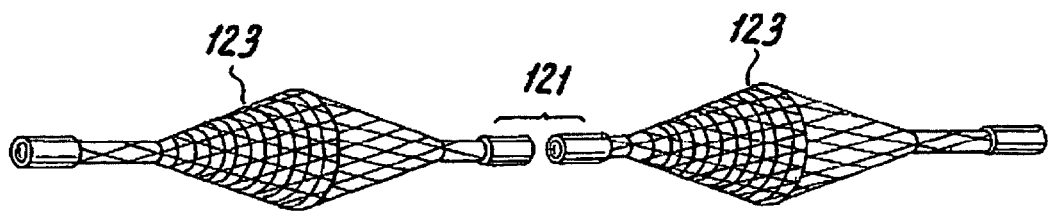
Figure 11E:
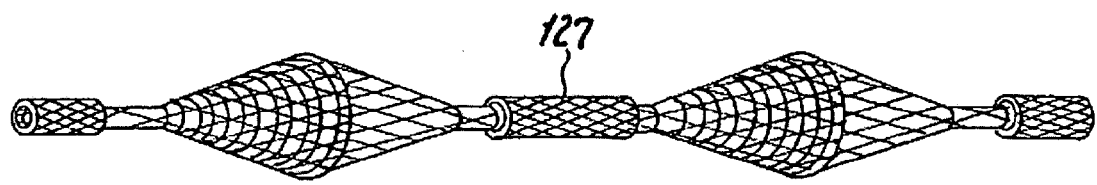
Figure 11F:
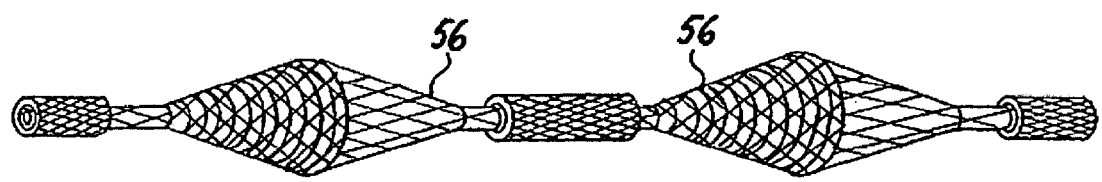
Figure 11G:
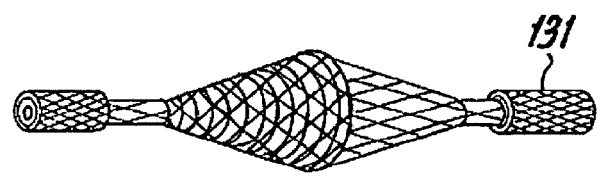

Referring now to FIGS. 8 and 9, fabrication of the filter 50 may be performed in accordance with a series of process steps as described below. Initially, a mandrel 96 (FIG. 8) with a series of molded forms 97 and 98 is prepared by selecting a mandrel of appropriate length, at step 100 (FIG. 9), and providing a plurality of crimps 101 (FIG. 8) on the mandrel at intervals of approximately two to three inches, at step 102. The process proceeds by placing molds over the crimps, at step 104, filling the molds with a dissolvable compound, at step 106, curing the compound, at step 108, and removing the molds, at step 110. Suitable materials for molding include water soluble plastics such as polyethylene oxide, chemical soluble plastics such as styrene or PVC, and other water soluble materials such as sugar cubes, or gypsum based compounds. Molded forms may be continuously fabricated along the length of the crimped mandrel sections to maximize production efficiency. Another suitable method envisioned is to individually form the molds and bond to straight mandrels.

Referring now to FIGS. 10 and 11a-g, following preparation of the mandrel 96, the mandrel itself is selected for the method of fabricating the filters, at step 112. The method progresses by selecting a braider, at step 114, and braiding the inner layer 54 (FIG. 11a), at step 116, over the mandrel form system. Because of the convenient serially connected system of forms on the mandrel, the braider progressively weaves a continuous layer of braid over the consecutively connected forms. After the braid is applied, the mandrel is removed from the braider, at step 118, so that a curable epoxy may be applied to define an adhesive joint 119 (FIG. 11b) along spaced apart sections of the braid between forms. This step bonds braid filaments together, at step 120, so that subsequent separation of the forms minimizes deformation of the braid.

A center section 121 (FIG. 11c) of each braid is then cut, at step 122, and a prefabricated filter 123 (FIG. 11d) installed over one side of each form, at step 124. The individual segments are then reconnected, at step 126, by splicing a section of heat shrink tubing 127 (FIG. 11e) over each severed joint.

After the segments are re-connected, the mandrel assembly is then re-installed into the braider for braiding of the outer basket 56 (FIG. 11f), at step 128. Following braiding, the mandrel is removed from the braider, at step 130, with the braid filaments bonded together to form a joint 131 (FIG. 11g), at step 132. The mandrel is then cut at approximately one millimeter on the outside end of the adhesive, at step 134. At this point, the molded form may be dissolved by an appropriate solvent, at step 136, and the mandrel removed, at step 138. Lastly, a polyimide sleeve is bonded, at step 140, to the end opposite the filter.

The alternative filter embodiment 80 may be fabricated similar to the procedure above with only minor variations. Conveniently, because of the composite nature and relatively high pic density of the metallic/polymeric braid, only one braiding step is required. After the final braid, the polymeric strands at the proximal end are mechanically or thermally cut away, and the filaments fused at the large diameter of the formed cone to form the collection cavity and to allow for greater blood flow.

In operation, the guide wire 30 may be advanced through a vascular system in any conventional manner to establish a path for the catheter to track over. Generally, as shown in FIG. 1, the guide wire is inserted through the lesion and disposed downstream of the lesion 24 a variably selected distance. The distance selected by the operator may be conveniently adjusted merely by further advancing or slightly withdrawing the guide wire. This provides the highly desirable capability of enabling the operator to independently adjust the selected distance to preclude the possibility of embolic material progressing through a branch path between the lesion and the filter. The catheter 20 is then inserted along the guide wire to access the treatment area. Typically, image scanning techniques aid in the exact positioning of the catheter relative to the lesion such that the lesion treatment device will have maximum effectiveness.

The filter may then be deployed by actuating an actuating mechanism (not shown) coupled to the core wire 34 for axially moving the shaft 38 relative to the core wire. As the shaft advances axially along the core wire in the distal direction, the filter basket 52, having its distal end 57 attached to the fixed core wire and its proximal end connected to the shaft, compresses axially and expands radially outwardly against the inner walls of the blood vessel. In its expanded state, the filter 50 collects any plaque that may have loosened and become dislodged from the treated area.

Once the treatment concludes, and the catheter is withdrawn from the body, the filter is retracted radially inwardly by shifting the shaft back to its original position. As the filter retracts, the collection cavity 62 traps any material strained against the filter layer. The guide wire itself is then carefully withdrawn from the vasculature.

Referring now to FIGS. 12 through 16, a temporary filter guide wire according to a further embodiment of the present invention is shown, and generally designated 200. The guide wire generally includes a proximal end 202 having an actuating mechanism 208, an intermediate portion 220 including a housed collapsible filter element 222, and a flexible distal end 240.

With particular reference to FIG. 12, the proximal end 202 includes a solid stainless steel core wire 204 having a diameter, for example, of approximately 0.0075 inches and slidably confined coaxially by an elongated shaft 206. The shaft may include, for example, an inner diameter of approximately 0.010 inches and an outer diameter of approximately 0.014 inches. The proximal tip of the core wire nests within the handle mechanism 208 that includes a rotatable handle element 209 having a formed central blind bore 210 and a threaded hollow shank 212. A fixed threaded base 214 having a throughbore 216 receives the proximal portion of the shaft 206 and rotatably engages the handle element to define the actuating mechanism.

Figure 14:
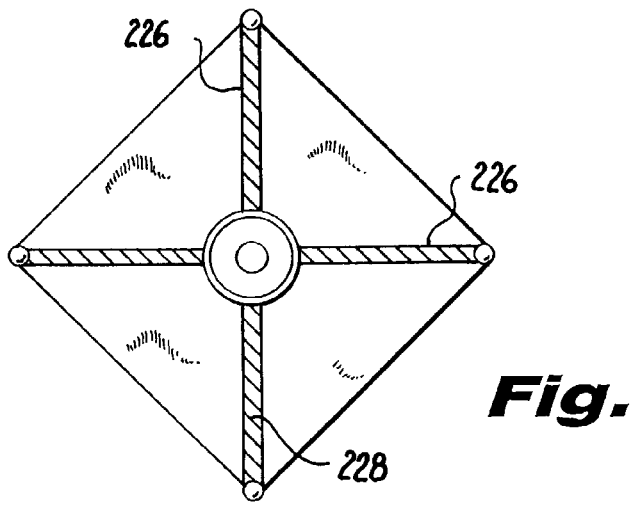
FIG. 14 is an axial view along line 14-14 of FIG. 13.
Figure 15:
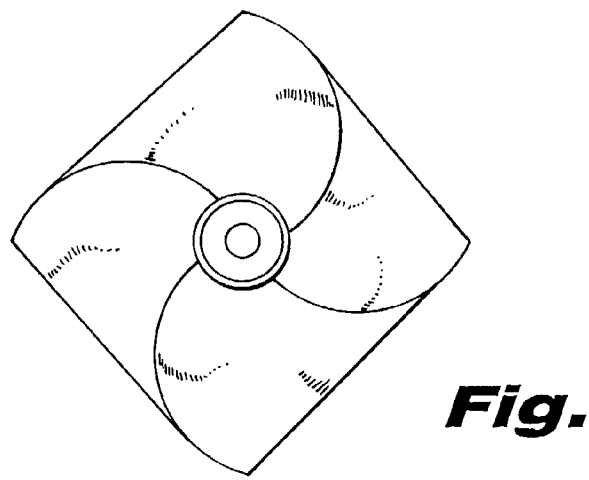
FIG. 15 is an axial view similar to FIG. 14 and showing an alternative strut arrangement.
Figure 16:
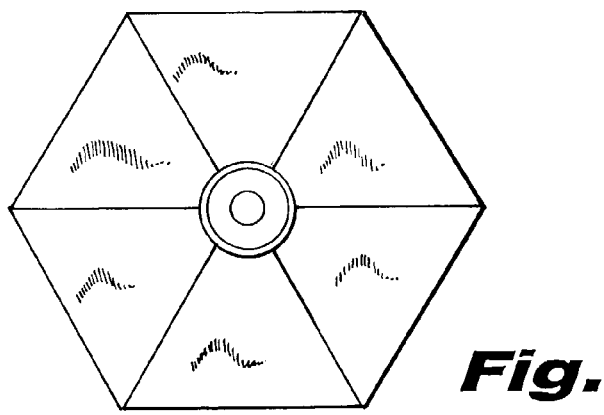
FIG. 16 is an axial view similar to FIG. 14 and showing an alternative strut arrangement.

Referring now to FIGS. 12 and 13, the core wire 204 and the shaft 206 extend longitudinally to define the intermediate portion 220 of the guide wire. The filter element 222 is mounted to the intermediate portion and includes an intermediate quad filar spring 224 of approximately 0.002 inch diameter wire that extends approximately three to seven centimeters from the end of the shaft, depending on the application. The respective ends of four wires comprising the quad spring are unwound, straightened, and outwardly biased approximately forty-five degrees from the spring axis at spaced apart radial locations to define a plurality of umbrella shaped filter struts 226. These struts form the support structure for the filter. As shown in FIGS. 14, 15, and 16, the strut spacing may conveniently take on a variety of configurations depending on the particular application desired. Lashed to the struts is a fine wire mesh 228 of approximately 0.001 inches thick within 40 to 500 micron pores for straining particulate matter from the bloodstream.

Further referring to FIG. 12, the radial exterior of the distal portion of the core wire 204 carries a bonded housing or pod 230 having an axially open mouth 232 slightly larger in diameter than the diameter of the filter in a closed configuration. The mouth opens into a cavity sufficiently sized to fully enclose the filter during insertion or withdrawal of the guide wire. The pod would also have a rounded inward edge at its proximal opening so as to envelop the filter when retracted and prevent unintentional engagement of a stent or catheter upon withdrawal. In an alternative embodiment, the housing 230 can include a reduced-in-diameter collar 260 radially affixed to the core wire proximate the distal end of the core wire. The pod may be fabricated out of a spring material wound in the opposing direction as the spiral struts to improve the sliding of the two surfaces. Other options include a lubricious plastic such as polyethylene.

FIG. 13a illustrates an alternative embodiment of the housing 230 in FIG. 13 in which the housing 230 is formed in a frusto-conical configuration including an oversized-in-diameter mouth opening axially outwardly from the core wire distal end and a reduced-in-diameter collar radially affixed to the core wire proximal of the core wire distal end.

The distal end 240 of the guide wire 200 comprises an extension of the core wire 204 from a bonded distal joint and surrounded by a distal spring member 242 that bonds to and projects outwardly from the distal side of the filter housing 230. The distal end terminates in a tip 244 that typically takes on a pre-formed "J" shape (not shown) for steering purposes through the vascular system.

Operation of the second embodiment proceeds in much the same way as that of the first embodiment, with the guide wire 200 first directed through the vasculature, followed by tracking with a treating catheter. Like the first embodiment, the guide wire 200 is advantageously adjustable in the blood vessel independent of the catheter, allowing a variable selected distance between the location of the stenosis and the filter. However, the way in which the filter 222 expands and retracts differs somewhat from the previously described embodiment.

With the handle mechanism 208 in a normally open configuration, the operator turns the rotatable element 209 to incrementally drive the core wire 204 axially with respect to the shaft 206. The relative axial displacement of the core wire causes the filter housing 230 to become disengaged from the filter struts 226. Because of the spring biased nature of the filter struts 226, as the filter exits the housing, the struts expand radially outwardly against the blood vessel wall such that the wire mesh spans the vessel diameter. In its extended state, the filer allows bloodflow to continue through the vessel while dislodged material becomes entrapped in the wire mesh for collection in the cavity.

Once the lesion treatment procedure is complete, and the necessity for filtering has completely diminished, the handle mechanism is actuated to pull the core wire back to its original position. This activity causes the housing mouth to re-engage the filter struts and urge the struts radially inwardly as the housing encloses the filter. With the filter fully retracted, the streamlined guide wire may be easily and safely withdrawn from the body.

Those skilled in the art will appreciate the many benefits and advantages afforded the present invention. Of relative importance is the feature that avoids any additional control wires, beyond the guide wire itself, in order to expand and retract the filter. Not only does this minimize the number of components necessary to practice the invention, but the angioplasty procedure itself is made safer for the patient.

Additionally, the present invention provides the capability of adjusting the distance between the filter and the catheter lesion treatment device in vivo, eliminating the need to withdraw the guide wire or catheter for distance adjustment should the relative spacing be inadequate.

The filter itself, in one embodiment, provides substantial manufacturability benefits by requiring only a single braiding step. Consequently, braiding additional filter layers adding to the device's complexity are eliminated. By minimizing the process steps required to fabricate the filter, costs involved in manufacture are greatly reduced.

Moreover, the method of fabricating filters according to the present invention offers added efficiencies in manufacture due to the production line processing scheme. Employing such a scheme serves to dramatically improve the throughput rate of filters to minimize overall costs.

While the invention has been particularly shown and described with reference to the preferred embodiments thereof, it will be understood by those skilled in the art that various changes in form and detail may be made therein without departing from the spirit and scope of the invention.

For example, the invention may be used in any intravascular treatment utilizing a guide wire where the possibility of loosening emboli may occur. Although the description herein illustrates angioplasty and stent placement procedures as significant applications, it should be understood that the present invention is in no way limited only to those environments.

What is claimed is:

1. A vascular filter guide wire for directing placement of a catheter with respect to a blood vessel lesion and filtering particulate matter dislodged by treatment of said vessel, said guide wire including:

an elongated flexible core wire having a proximal end and a distal end, said elongated flexible core wire being insertable and steerable through a patient's vasculature to a position downstream of said lesion;

a tubular flexible shaft slidably disposed along said core wire, said shaft including a proximal portion and a distal portion disposed proximally of said core wire distal end for placement downstream of said lesion; and a collapsible filter coupled at its proximal end to said distal portion of said shaft and at its distal end to said core wire, said filter operable in response to the relative displacement between said shaft and said core wire to radially extend outwardly within said vasculature and trap particulate matter arising from the treatment of said lesion, the filter including an inner braid layer and an outer braid layer, each layer extending from the filter proximal end to the filter distal end, the inner braid layer rotationally fixed relative to the outer braid layer.

2. The vascular filter guide wire according to claim 1, wherein said filter includes a braid comprising a composite metallic/polymeric material, said material including a plurality of metallic filaments to define a support structure and a polymeric mesh interwoven with said metallic filaments to define a strainer.

3. The vascular filter guide wire according to claim 2, wherein said metallic filaments have respective common proximal and distal halves, and wherein said polymeric mesh is interwoven in said distal half of said metallic filaments.

4. The vascular filter guide wire according to claim 3, wherein the pic density of the interwoven metallic filaments and polymeric mesh results in a spacing of approximately 40 microns to approximately 500 microns.

5. The vascular filter guide wire according to claim 2, wherein said plurality of metallic filaments and said polymeric mesh are woven at a ratio of approximately 1:4.

6. The vascular filter guide wire according to claim 1, wherein a filter mesh is disposed between the inner and outer braid layers.

7. The vascular filter guide wire according to claim 6, wherein the mesh includes pores in the range of approximately 50 microns to approximately 400 microns.

8. The vascular filter guide wire according to claim 6, wherein the filter includes a proximal portion and a distal portion, the mesh positioned in the distal portion.

9. The vascular filter guide wire according to claim 8, wherein in a radially extended configuration, the proximal portion and distal portion of the filter have a generally conical shape facing in opposite directions, together forming essentially a diamond shape.

10. The vascular filter guide wire according to claim 1, wherein the distal portion of the shaft is disposed between the inner braid layer and the outer braid layer and bonded thereto.

11. The vascular filter guide wire according to claim 1, further comprising a flexible coil spring coaxially surrounding the core wire distal end, the core wire distal end including an annular shoulder, the coil spring mounted at a proximal end thereof to the shoulder.

12. The vascular filter guide wire according to claim 11, wherein the core wire distal end includes a tapered portion having a distal end attached to a hemispherically shaped tip, the coil spring mounted at a distal end thereof to the hemispherically shaped tip.

13. The vascular filter guide wire according to claim 11, wherein the filter distal end abuts the coil spring.

14. The vascular filter guide wire according to claim 1, wherein the filter comprises a cylindrical section.

15. The vascular filter guide wire according to claim 14, wherein the cylindrical section includes longitudinal pleats.

16. The vascular filter guide wire according to claim 15, wherein the filter further comprises a flared proximal end and a closed distal end, the cylindrical section disposed therebetween.

17. The vascular filter guide wire according to claim 16, wherein the flared proximal portion includes a first and second section having generally conical shapes facing in opposite directions, together forming essentially a diamond shape.

18. The vascular filter guide wire according to claim 16, wherein the closed distal end has a generally conical shape with a base of the conical shape connected to the cylindrical section.

19. The vascular filter guide wire according to claim 14, wherein a filtering medium is disposed in the cylindrical section.

20. The vascular filter guide wire according to claim 1, wherein the core wire includes a wave-shaped proximal end.

21. The vascular filter guide wire according to claim 1, wherein the shaft comprises a polyimide tube or a hypotube.

22. The vascular filter guide wire according to claim 1, wherein an outer diameter of the shaft is approximately equal to a nominal diameter of the guidewire.

23. The vascular filter guide wire according to claim 1, wherein an inner diameter of the shaft is friction fit with the core wire proximal end.

24. The vascular filter guide wire according to claim 1, wherein the filter includes supports that are compressible inwardly to radially retract the filter.

25. The vascular filter guide wire according to claim 1, wherein the proximal end of the filter is adhesively bonded or soldered to the distal end of the shaft.

26. A vascular filter guide wire for directing placement of a catheter with respect to a blood vessel lesion and filtering particulate matter dislodged by treatment of said vessel, said guide wire including:

an elongated flexible core wire insertable and steerable through a patient's vasculature to a position downstream of said lesion;

a tubular flexible shaft disposed along said core wire;

a collapsible filter coupled at its proximal end to said shaft and being operable to radially extend outwardly within said vasculature in order for said filter to trap particulate matter arising from the treatment of said lesion, the filter including an inner braid layer and an outer braid layer, each layer extending from the filter proximal end to the filter distal end, the inner braid layer rotationally fixed relative to the outer braid layer.

27. A filtering device, comprising a guide wire insertable and steerable through a patient's vasculature, the guide wire including a generally tubular shaft coaxially disposed about a core wire, a distal end of the shaft positioned proximal of a distal end of the core wire, and a filter having a proximal end coupled to the shaft distal end and a distal end coupled to the core wire, the filter including an inner braid layer and an outer braid layer, each layer extending from the filter proximal end to the filter distal end, the inner braid layer rotationally fixed relative to the outer braid layer, the filter operable between a collapsed configuration and an expanded configuration via longitudinal movement of the shaft with respect to the core wire.

28. The filtering device according to claim 27, further comprising a flexible coil spring coaxially mounted to the core wire, wherein the filter distal end abuts the flexible coil spring.

29. The vascular filter guide wire according to claim 28, wherein the core wire distal end includes a tapered portion having a distal end attached to a hemispherically shaped tip, the coil spring mounted at a distal end thereof to the hemispherically shaped tip.

30. The vascular filter guide wire according to claim 27, wherein a filter mesh is disposed between the inner and outer braid layers.

31. The vascular filter guide wire according to claim 30, wherein the mesh includes pores in the range of approximately 50 microns to approximately 400 microns.

32. The vascular filter guide wire according to claim 30, wherein the filter includes a proximal portion and a distal portion, the mesh positioned in the distal portion.

* * * * *